(12) United States Patent
Giraud et al.

(10) Patent No.: US 10,137,054 B2
(45) Date of Patent: Nov. 27, 2018

(54) MASSAGE DEVICE EQUIPPED WITH INTERCHANGEABLE MASSAGE HEADS

(71) Applicant: SEB S.A., Ecully (FR)

(72) Inventors: Camille Giraud, Lyons (FR); Franck Mandica, Francheville (FR)

(73) Assignee: SEB S.A., Ecully (FR)

( * ) Notice: Subject to any disclaimer, the term of this patent is extended or adjusted under 35 U.S.C. 154(b) by 868 days.

(21) Appl. No.: 14/087,573

(22) Filed: Nov. 22, 2013

(65) Prior Publication Data

US 2014/0142472 A1 May 22, 2014

(30) Foreign Application Priority Data

Nov. 22, 2012 (FR) .................... 12 61107

(51) Int. Cl.
| A61H 15/00 | (2006.01) |
| A61H 15/02 | (2006.01) |
| A61H 23/02 | (2006.01) |
| A61H 7/00 | (2006.01) |
(Continued)

(52) U.S. Cl.
CPC ......... *A61H 15/0085* (2013.01); *A61H 7/005* (2013.01); *A61H 7/007* (2013.01); *A61H 15/02* (2013.01); *A61H 23/0245* (2013.01); *A61H 2015/0014* (2013.01); *A61H 2015/0057* (2013.01); *A61H 2201/0107* (2013.01); *A61H 2201/10* (2013.01); *A61H 2201/105* (2013.01); *A61H 2201/1654* (2013.01); *A61H 2201/1685* (2013.01); *A61H 2201/5007* (2013.01); *A61H 2201/5058* (2013.01); *A61H 2201/5092* (2013.01); *A61H 2205/022* (2013.01); *A61N 1/30* (2013.01); *A61N 2005/0659* (2013.01); *A61N 2005/0663* (2013.01)

(58) Field of Classification Search
CPC ................ A61H 7/005; A61H 9/0007; A61H 9/0021–9/0028; A61H 33/6036; A61M 35/00; A61M 35/003
See application file for complete search history.

(56) References Cited

U.S. PATENT DOCUMENTS 1,577,751 A * 3/1926 Paschall ................. A61H 7/004
15/22.1
4,127,116 A * 11/1978 Pannetier ........... A61H 15/0085
601/125
(Continued)

FOREIGN PATENT DOCUMENTS

| CN | 201750912 U | 2/2011 |
| EP | 1925275 B1 | 11/2011 |
| WO | 2010012857 A1 | 2/2010 |

*Primary Examiner* — Valerie L Woodward
(74) *Attorney, Agent, or Firm* — The Webb Law Firm

(57) ABSTRACT

The invention concerns massage device including body which contains drive mechanism, at least one type of massage head which includes massage elements, a transmission mechanism which allows the activation of the massage elements under the action of the drive mechanism, installation mechanism which are configured to be installed on and uninstall from the body at least one type of massage head. In accordance with the invention, the device includes recognition means of the type of massage head installed on the body and control mechanisms for said massage device based on the recognition of the type of massage head.

20 Claims, 6 Drawing Sheets

(51) Int. Cl.
*A61N 1/30* (2006.01)
*A61N 5/06* (2006.01)

(56) References Cited

U.S. PATENT DOCUMENTS

| | | | | |
|---|---|---|---|---|
| 4,526,163 A * | 7/1985 | Fedders | ................ | A61H 7/004 601/112 |
| 4,733,655 A * | 3/1988 | Smal | ................ | A61H 7/005 601/133 |
| 4,920,957 A * | 5/1990 | Sutherland | ............ | A61H 7/005 601/101 |
| 5,103,809 A * | 4/1992 | DeLuca | ................ | A61H 7/001 601/133 |
| 5,685,827 A * | 11/1997 | Shimizu | ............ | A61H 15/0085 601/112 |
| 6,032,313 A * | 3/2000 | Tsang | ................ | A46B 13/02 15/21.1 |
| 6,251,089 B1 * | 6/2001 | Kuznets | ................ | A61H 7/005 601/112 |
| 8,777,881 B2 * | 7/2014 | Tsai | ................ | A61H 7/004 601/112 |
| 2002/0107459 A1 * | 8/2002 | Chang | ................ | A61H 7/005 601/97 |
| 2004/0158179 A1 * | 8/2004 | Chen | ................ | A61H 7/005 601/87 |
| 2008/0125682 A1 * | 5/2008 | Bonneyrat | ............ | A61H 7/00 601/112 |
| 2008/0183251 A1 * | 7/2008 | Azar | ................ | A61B 18/18 607/101 |
| 2008/0200861 A1 * | 8/2008 | Shalev | ................ | A61Q 9/04 604/20 |
| 2008/0209650 A1 | 9/2008 | Brewer et al. | | |
| 2008/0306415 A1 * | 12/2008 | Chan | ................ | A61H 15/0085 601/93 |
| 2009/0306577 A1 * | 12/2009 | Akridge | ............ | A61M 35/003 604/20 |
| 2010/0049177 A1 * | 2/2010 | Boone, III | ............ | A61H 9/0057 606/9 |
| 2011/0015463 A1 * | 1/2011 | Legendre | ............ | A45D 40/00 600/9 |
| 2012/0165710 A1 * | 6/2012 | Nichols | ................ | A61H 7/005 601/72 |

* cited by examiner

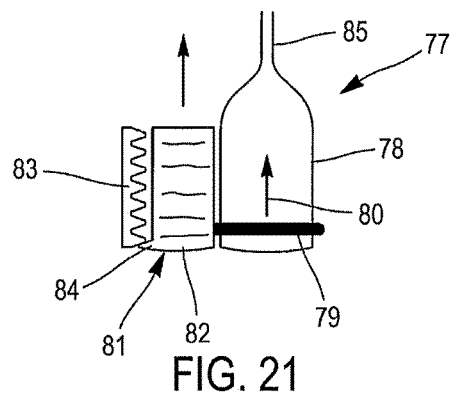
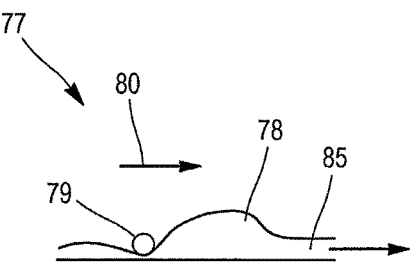
FIG. 21    FIG. 22
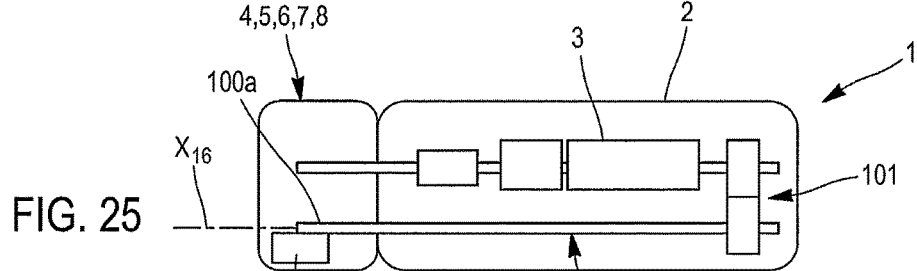
FIG. 25
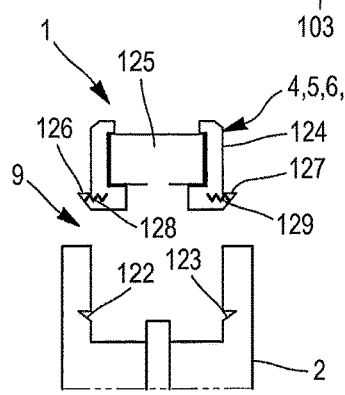
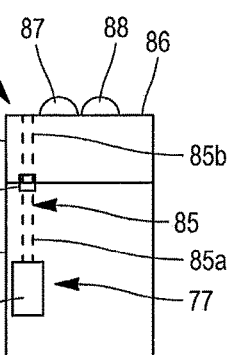
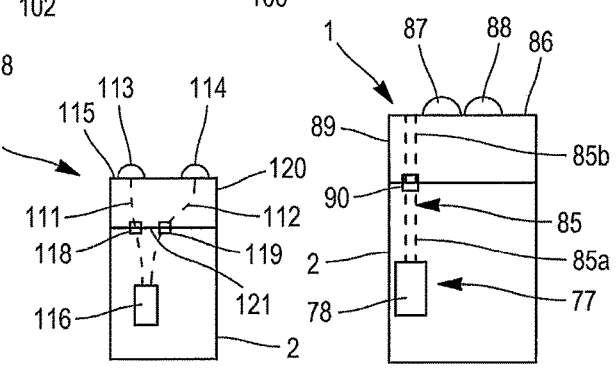
FIG. 4    FIG. 27    FIG. 28
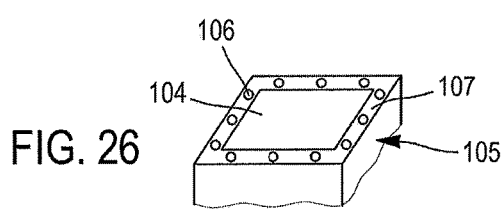
FIG. 26

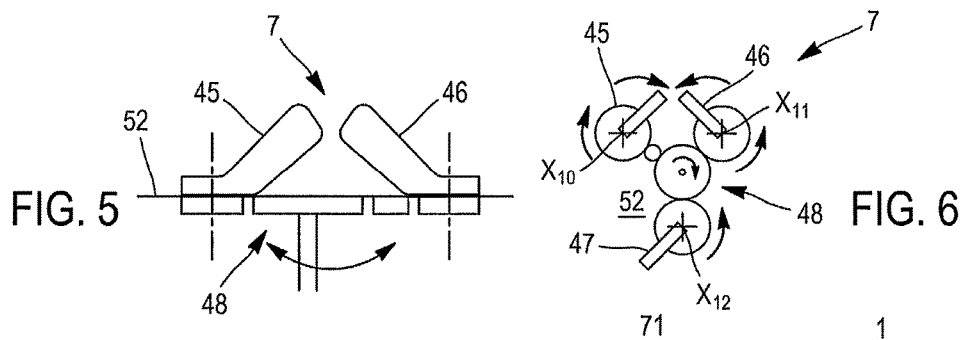
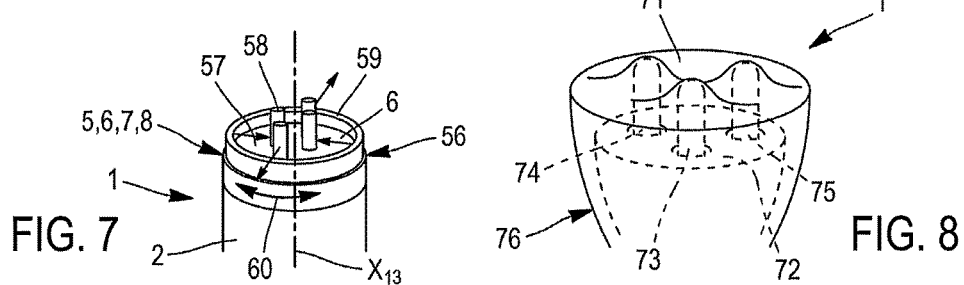
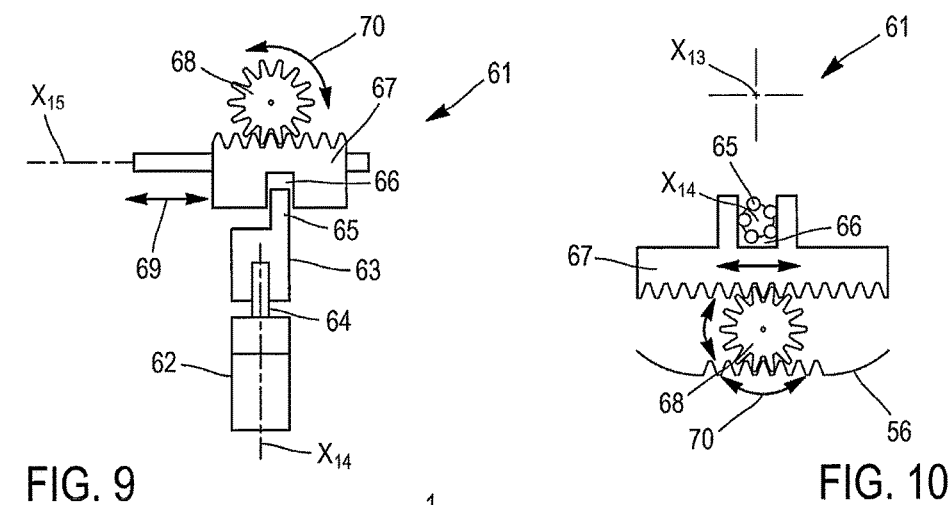
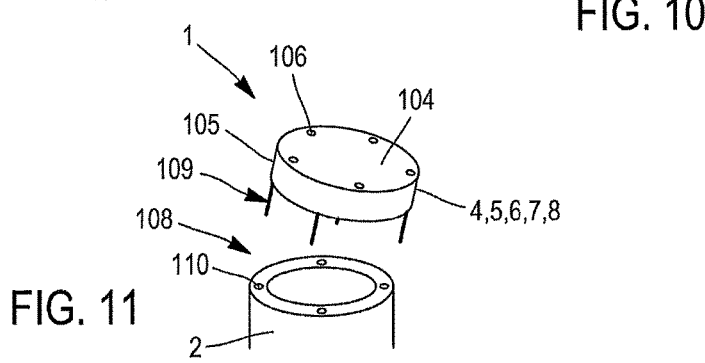

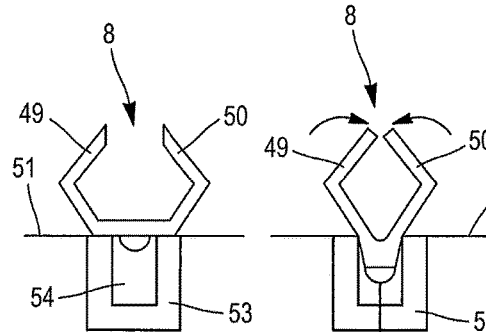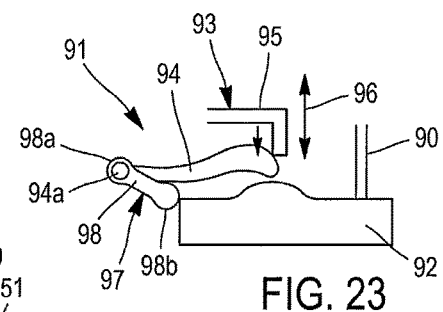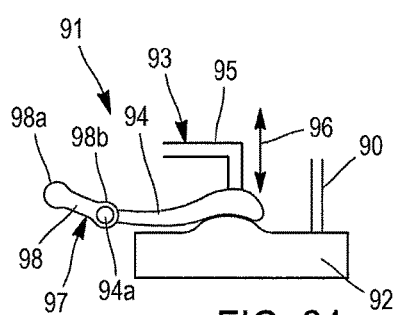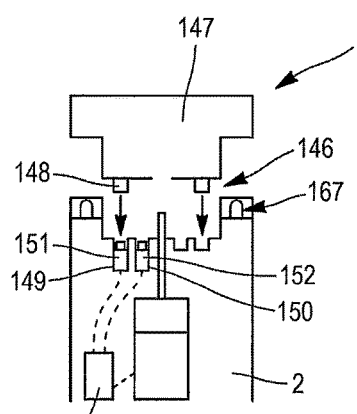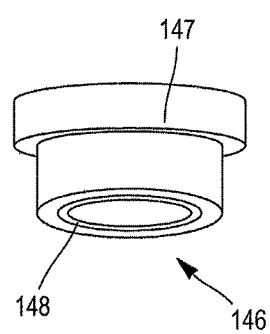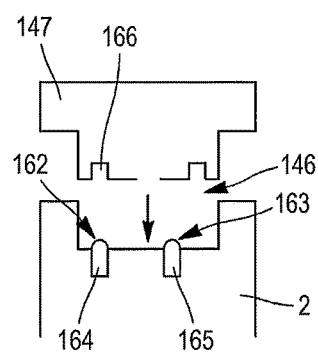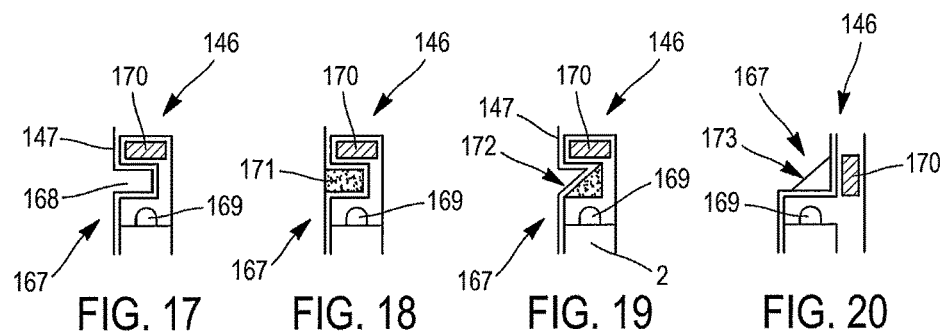

MASSAGE DEVICE EQUIPPED WITH INTERCHANGEABLE MASSAGE HEADS

CROSS-REFERENCE TO RELATED APPLICATION

This application claims priority to French Patent Application No. 1261107 filed Nov. 22, 2012, the disclosure of which is hereby incorporated by reference in its entirety.

FIELD OF THE INVENTION

This invention concerns the domain of equipment for treating skin, in particular, on the face. The device in accordance with the invention allows, at a minimum, the skin to be massaged to improve its tone. A massage device in accordance with the invention may be used in households whose members wish to improve their appearance by changing, firming and rejuvenating their skin, in particular, on the face.

BACKGROUND OF THE INVENTION

Skin massage equipment generally consists of a body with a motor and a massage head which consists of massage elements configured to be activated by the motor through a transmission mechanism. Current prior art, in particular, patent EP 1 925 275 B 1 which, in addition to the aforementioned characteristics, discloses an installation mechanism and a transmission mechanism which allows the massage head to be easily replaced with a new or different one, where, in addition, the design of the transmission mechanism allows the head to be installed on the body with a slightly different angle of orientation of the head axis from the axis of the body.

The purpose of this invention is to design a skin massage device which allows various different types of massage heads to be installed on the body of the massage device, while optimizing the performance and characteristics of the massage device to improve its operation based on the type of massage head used.

SUMMARY OF THE INVENTION

To this end, the invention concerns a massage device with a body which contains a drive mechanism, at least one type of massage head with massage elements, a transmission mechanism which allows the activation of the massage elements under the action of the drive mechanism and installation mechanism which are configured to install at least one type of massage head in a removable manner on the body. Accordingly, the massage device in accordance with the invention allows the massage head to be easily and quickly replaced with another identical or different one. In accordance with the invention, the device includes a means to recognize the type of massage head installed on the body and control mechanisms for said massage device based on the recognition of the type of massage head. Accordingly, the device allows the detection of the type of head installed on the body and to change its operation based on the type of massage head by, for example, changing the speed of the drive mechanism by controlling elements of the drive mechanism or other items.

This allows massage heads with very different operational characteristics to be accommodated.

In accordance with an initial implementation of the massage device covered by the invention, the recognition means are mechanical sensors installed on at least one type of massage head and the body which are configured to transfer information to the control mechanisms based on the type of massage head installed on the body. Mechanical sensors cover any mechanical sensor, including electrical detectors, which come into contact with one another when the massage head is installed on the device.

In accordance with a second implementation of the massage device covered by the invention, the recognition means are magnetic sensors installed on at least one type of massage head and the body which are configured to transfer information to the control mechanisms based on the type of massage head installed on the body.

In accordance with a third implementation of the massage device covered by the invention, the recognition means are optical sensors installed on at least one type of massage head and the body which are configured to transfer information to the control mechanisms based on the type of massage head installed on the body.

Of course, other implementations of the recognition means are possible on the massage device without falling outside the scope of the invention.

In accordance with the massage device covered by the invention, the control mechanisms are configured to control the drive mechanism and change its action based on the type of massage head installed on the body. Accordingly, for example, the activation speed of the massage elements of the massage head may be changed, which optimizes the conditions for using the massage head.

This also allows drive mechanisms of greater or lesser complexity to be installed on the body, which are configured to activate various types of massage heads with very different design characteristics and control these drive mechanism based on the recognition of the massage head.

The massage device covered by the invention includes a wave emission system installed on the body, wave transfer means and an emission system to the massage head installed on the body. That allows skin treatment functions in addition to those of massage heads. These waves may be electromagnetic waves, in particular light, visible or infrared, or may be sonic, e.g., ultrasound. This also allows additional treatment of the user's skin. In an envisioned type of implementation, these waves consist or red or orange light. In a preferential but not limitative implementation, the massage device includes a light system installed on the body and the means to transfer light from the light system to the massage head.

In accordance with the massage device covered by the invention, the control mechanisms are configured to act on the wave emission system and alter the waves based on the type of massage head installed on the body.

In accordance with the massage device covered by the invention, it includes a system to distributed cosmetic products installed on the body and means to transfer the product from the body to the massage head. That allows skin treatment functions in addition to those of the massage heads. Depending on distribution system configuration, the cosmetic product may be distributed naturally, manually and/or automatically.

In one implementation, the massage device in accordance with the invention includes a means to trigger a cosmetic product distribution system which is configured to allow the operation of said distribution system in manual or automatic mode. That allows the massage device to be used in many ways; the user may, therefore, select a cosmetic treatment in addition to that achieved with the massage head.

In accordance with the massage device covered by the invention, the control mechanisms are configured to act on the cosmetic product distribution system and alter the distribution of the cosmetic product based on the type of massage head installed on the body. This allows cosmetic treatment suited to various massage heads.

In accordance with the massage device covered by the invention, the installation mechanism include a system to detect the correct installation of the massage head on the body. This ensures proper use of the massage device.

In accordance with the massage device covered by the invention, it includes interconnection mechanisms between the drive mechanism and the transmission mechanism configured to adjust the angle of orientation of the transmission mechanism compared to using a motor when the massage head is installed on the body. Accordingly, it is possible to install massage heads on the body at different angles; for example, certain massage heads may for be positioned along as an extension of the body during installation, while other heads may be positioned at a 45° angle to the body.

In accordance with one implementation of the massage device covered by the invention, one massage head type contains an application surface and the massage elements consist of at least two massage nozzles which extend perpendicularly to the exterior of the application surface, the massage nozzles are located on the application surface in virtual concentric circles with a center C, in which the transmission mechanism is configured to move the massage nozzles closer and/or, inversely, to move the massage nozzles further away by shifting said massage nozzles in one direction and/or another depending on their patterns around center C. This type of massage head allows the skin to be pinched.

In accordance with one implementation of the massage device covered by the invention, one massage head type contains an application surface and the massage elements consist of two massage nozzles which extend perpendicularly to the exterior of the application surface and the transmission mechanism is configured to rotate on an axis perpendicular to the application surface while oscillating the two nozzles. This type of massage head allows precision work around the eyes and mouth while, in particular, applying the massage nozzles perpendicularly to the skin to achieve a rotating pinching effect, or parallel to the skin to achieve a sculpting, tension effect.

In accordance with one implementation of the massage device covered by the invention, the massage head contains an application surface and the massage elements consist of three massage nozzles inclined toward the exterior relative to the application surface and the transmission mechanism is configured to rotate or oscillate the three massage nozzles along three, fixed axes which are perpendicular to the application surface. This type of massage head allows the skin to be lightly pinched.

In accordance with one implementation of the massage device covered by the invention, the massage head includes an application surface and the massage elements consist of at least two massage fingers which extend along the exterior of the application surface, where the massage fingers and the transmission mechanism are configured to form a claw. This type of massage head allows the skin to be pinched.

In accordance with various other implementations of the massage device covered by the invention, with massage nozzles or massage fingers, the massage head includes a soft skin which covers the massage elements. That avoids having the massage nozzles or massage fingers act too aggressively and allows a better grip of the skin due through surface contact.

In accordance with one implementation of the massage device covered by the invention, the massage head includes a crown which extends perpendicularly to the application surface and the transmission mechanism is configured to oscillate the crown around an axis perpendicular to the application surface. That allows a better grip of the skin and for complex movements to be made on the skin, in combination with the massage nozzles or massage fingers.

In accordance with one implementation of the massage device covered by the invention, the massage head includes an application surface and the massage elements consist of two massage wheels installed along two parallel longitudinal axes, with a gap between them, which extend partially outside the application surface where the transmission mechanism rotates the two wheels in a synchronized manner and in opposite directions so that, on plane perpendicular to the two axes, the section of the massage wheel on the left which extends outside of the application surface turns counterclockwise and the section of the massage wheel on the right which extends outside the application surface turns clockwise. This type of massage head allows the skin to be folded.

In accordance with the massage device covered by the invention, it includes a trans-dermal ionization treatment mechanism which is configured to transfer an electric current to the skin during the application of said massage device to increase and/or accelerate penetration of a cosmetic product which may either be distributed by the cosmetic product distribution system described above or applied directly to the skin by the user. Ionization is a process which was initially developed for the application of drugs to the skin, in particular for sports medicine, but is also appropriate to best insure penetration of cosmetic products. In one implementation, this trans-dermal ionization treatment mechanism includes two electrodes with different electrical potentials which may be installed on the massage nozzles or wheels and/or on the application surface of the massage head. The settings of the massage device in accordance with the invention allow, in particular when it also includes a products cosmetic distribution system, trans-dermal ionization treatment prior to and/or during the application of the cosmetic product. These settings depend on the recognition of the massage head installed on the body.

BRIEF DESCRIPTION OF THE DRAWINGS

The following description highlights the characteristics and benefits of this invention and refer to the diagrams, including:

FIG. 4 shows a removable installation system between the massage head and the body;

FIGS. 5 and 6 show a massage head which includes three inclined nozzles;

FIG. 7 shows a crown on the massage head;

FIG. 8 shows a soft skin on the massage head;

FIGS. 9 and 10 show a transmission mechanism between the massage head and the body;

FIG. 11 shows a fiber optic connection system between the massage head and the body;

FIGS. 12 and 13 show a massage head variation with claws;

FIGS. 14 to 16 show variants of massage head recognition means on the body;

FIGS. 17 to 20 show variants of optical sensor massage head recognition means on the body;

FIGS. 21 and 22 show a cosmetic product distribution system;

FIGS. 23 and 24 show a variation of the cosmetic product distribution system;

FIG. 25 shows a vibration system on the massage device;

FIG. 26 shows luminescent diodes on the massage head;

FIG. 27 shows a trans-dermal ionization treatment mechanism on the massage device;

FIG. 28 shows a distribution system installed between the body and the massage head;

DESCRIPTION OF THE INVENTION

Figure 1:
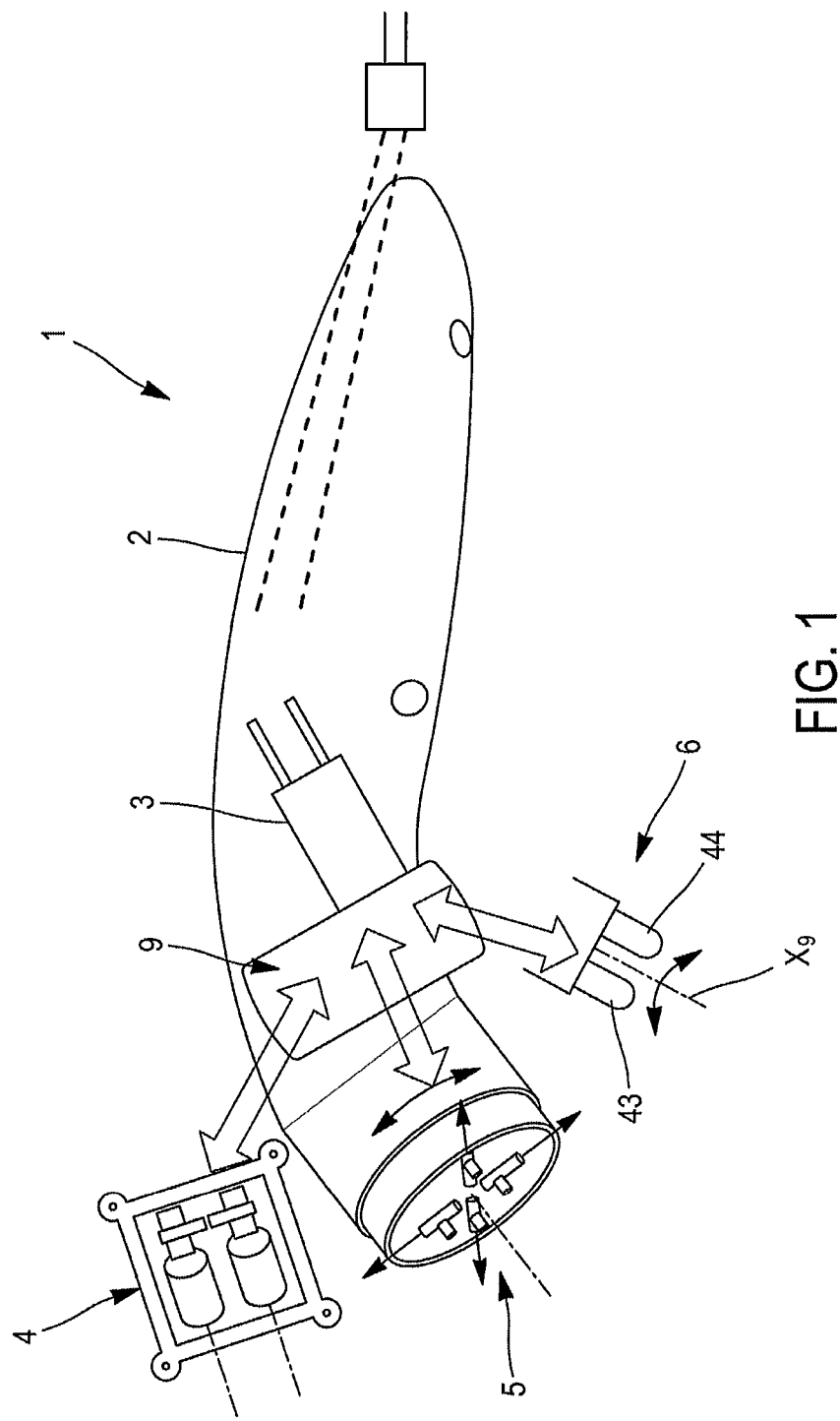
FIG. 1 shows a massage device in accordance with the invention on which various massage head designs may be installed.

As shown in FIG. 1, massage device 1 includes body 2 inside of which motor 3 is installed which is electrically powered by a connection either to an external electrical source (an electrical outlet and low voltage transformer), or to an internal electrical source (rechargeable or disposable batteries). Massage device 1 also includes a reduction gear installed on the output of motor 3 to reduce its rotation speed and adjust it to the type of use. Massage device 1 is configured to allow the connection of various types of massage heads 4, 5, 6, 7 and 8 shown in FIGS. 1, 2, 3, 5, 6, 12 and 13. To do so, the massage device includes removable connection mechanisms 9 between body 2 and massage heads 4, 5, 6, 7 and 8.

Figure 2:
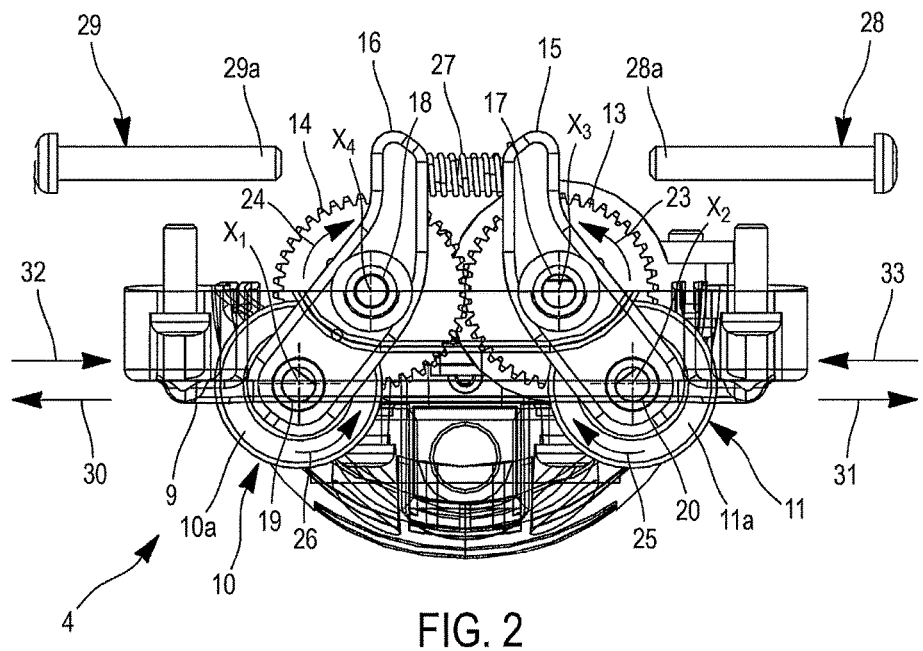
FIG. 2 shows a massage head which includes massage wheels.

In FIG. 2, massage head 4 includes application surface 9 and two massage wheels 10 and 11 of which sections 10a and 11a extend outside application surface 9. These wheels 7 and 8 are distributed along two axes X1 and X2, which are parallel to one another. In accordance with this implementation, motor 3 includes a drive shaft connected to gear 13. Accordingly, motor 3 rotates gear 13 along axis X3. This gear 13 meshes with another gear 14 with an identical design located along axis X4.

As shown in FIG. 2, massage head 4 includes two supports 15 and 16. These supports 15 and 16 are shown in a pivoting connection around axes X3 and X4, respective, using two drives 17 and 18. These supports accept wheels 10 and 11 in a pivot connection with axis X1 and X2 to using two drives 19 and 20 mounted in a pivot connection on said supports 15 and 16.

Massage head 4 includes two other gears with an identical design (not shown). One of the gears is driven by wheel 11 through the drive 20, for example, to using flutings (not shown) installed between these elements and meshes with gear 13. Similarly, the other gear is driven by wheel 10 through drive 19 and, meshes with gear 14. Accordingly, when gear 13 is driven by motor 3, which turns in the direction of the arrow 23, gear 14 turns in the direction of arrow 24, which causes wheel 10 to be driven in the direction of arrow 26 and wheel 11 in the direction of arrow 25.

As shown in FIG. 2, springs 27 are installed between two supports 15 and 16. In an initial position, these springs 27 act against supports 15 and 16 and push them against extremities 28a and 29a of two adjustment screws 28 and 29 installed on massage head 4. Accordingly, in the initial position, wheels 10 or 11 are held apart from one another with a minimal gap. Further, adjustment of the screws 28 and 29 allows the minimal gap between these two wheels 7 and 8 to be changed. When sections 10a and 11a of wheels 10 and 11 are applied on the skin, the opposite rotation of wheels 10 and 11 in the direction of arrows 25 and 26 forms a fold in the skin. The action by the skin on these wheels, when that action is greater than the action exercised by springs 27, compresses these springs 27 and separates the wheels in the direction of arrows 30 and 31 shown in FIG. 2. On the other hand, if the action exercised by the skin on wheels 10 and 11 is less than the action exercised by springs 27, these springs 27 extend and force wheels 10 and 11 in the direction of arrows 32 and 33 shown in FIG. 2, until reach a position of balance in reached.

Variants of the implementation of the transmission mechanisms on installation head 4, which operates in accordance with the same principle, are possible without falling outside the scope of the invention.

Figure 3:
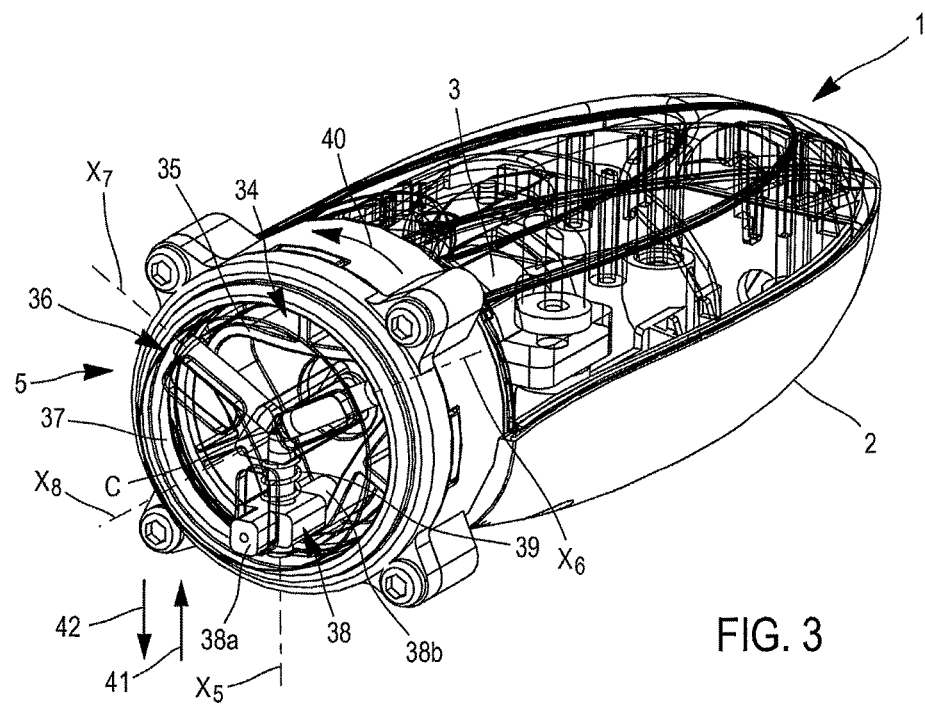
FIG. 3 shows a massage head which includes massage nozzles.

As shown in FIG. 3, the variation of massage head 5 includes transmission piece 34 which contains triangular cam 35. Cylindrical guide piece 36 has application surface 37 which is positioned parallel to the surface of the skin when massage device 1 is used.

Only one massage nozzle 38 is shown on this FIG. 3. With respect to this FIG. 3, it is understand in accordance with this implementation includes that massage head 5 three, identical uniformly distributed massage nozzles. Massage nozzle 38 includes external section 38a which extends perpendicularly to application surface 37, to the exterior of it. This external section 38a comes into contact with the user's skin when massage device 1 is applied.

As shown in FIG. 3, guide piece 36 can be installed along axis X5 on guide piece 36. The same applies to the nozzles along axes X6 and X7. Motor 3 rotates guide piece 36 along axis X8.

As shown in FIG. 3, massage nozzle 38 includes internal section 38b. When massage head 5 is installed on body 2, this internal section 38b is positioned inside cam 35 of transmission piece 9. This internal section 38b is maintained in support against cam 35 by spring 39. When guide piece 36 is rotated along axis X8 in the direction of arrow 40, massage nozzle 38 turns with it. Cam 35 acts against internal section 69 and pushes massage nozzle 38 in the direction of arrow 41 to an initial angled section, which moves massage nozzle 21 along axis X5 in the direction of arrow 41 to center C, which is the intersection of axis X8 with axes X5, X6, X7. Then, a second angled section, cam 35 ceases to act against internal section 38b. Spring 39, which acts as a return, pushes against massage nozzle 38 in the direction of arrow 42, thereby moving it along axis X5 in the direction of this arrow 42 to distance it from center C. Therefore, the rotation of guide piece 36 around axis X8 combined with the movement of massage nozzle 38 along axis X5 allows this massage nozzle 38 to approach then move away from center C in a circular or curvilinear pattern. It is understood that the two other massage nozzles make the same movements in synchronization with massage nozzle 38. Accordingly, the three massage nozzles 38 are located along the same virtual circle of center C and move in a curvilinear pattern around center C. That creates a turning pinch of the skin using massage head 5.

Variants of implantation with four nozzles are possible for massage head 5. A fixed guide piece and a transmission piece rotating around axis X8 could also be envisaged, in which case the massage nozzles would move to center C toward and away from it in a radial pattern. There are also multiple variants of cams based on the number of nozzles present.

Other variants of massage heads are possible. In FIG. 1, massage head 6 is shown with two nozzles 43 and 44 which rotate or oscillate around axis X9 through motor 3 and a transmission mechanism.

In FIGS. 5 and 6, massage head 7 includes three massage nozzles 45, 46 and 47 which are rotated around axes X10, X11 and X12 by gearing mechanism 48. These massage nozzles 45, 46 and 47 are inclined to application surface 52.

In FIGS. 12 and 13, massage head 8 includes two claws 49 and 50 which extend to the exterior of application surface 51. These claws 49 and 50 are soft. Massage head 8 includes rigid piece 53 with partition 54 in which may penetrate claws 49 and 50 which deform since they are flexible and can close. Claws 49 and 50 are moved inside partition 54 by a traction mechanism in the direction of arrow 55. The flexibility of claws 49 and 50 allows them to return to a spread position when the traction mechanism allows claws 49 and 50 to move in the opposite direction of arrow 55.

In a variation shown in FIG. 7, massage device 1 includes crown 56 which may be installed with massage heads 5, 6, 7 and 8 with nozzles or claws. In FIG. 7, nozzles 58 are shown. This crown 56 rotates along axis X13 and extends beyond application surface 57 so that the extremities of massage nozzles 58 are located on the same plane as peripheral edge 59 of crown 56. This crown 56 preferably rotates with an alternative movement around axis X13 in the direction of arrow 60. To do so, massage device 1 includes transmission mechanism 61 shown in FIGS. 9 and 10. This transmission mechanism 61 includes reduction gear 62 which is located in body 2 of massage device 1. This reduction gear 62 may be different or the same as the reduction gear of motor 3. It may also be driven by the same motor 3 through a gearing system (not shown) or even by an independent motor located in body 2. Eccentric gear 63 is installed on drive 64 of reduction gear 62. This eccentric gear 63 includes finger 65 is offset to axis X14 of rotation of drive 64. This finger 65 is positioned in groove 66 installed on rack 67 mounted to move along axis X15 and gear with gable 68 which itself meshes with crown 56, as shown in FIGS. 9 and 10. Accordingly, finger 65 has a certain degree of freedom in groove 66 when rotating around axis X14, which allows an alternating motion to be transferred in the direction of arrow 69 to the rack and, therefore, an alternating motion in the direction of arrow 70 to gable 68 and crown 56. The benefit of this mechanism transmission 61 is to easily change the angle of incline between finger 65 and groove 66, which allows a massage head to be easily installed on body 2 at different angles, for example, along the axis of body 2 or at a 45-degree incline to body 2. Connection mechanisms are thereby created which allow the angles between the massage head and the body to be adjusted. Such a connection may be used with variants of the transmission mechanism between the massage head and the body, depending on the purpose. Connection variants can also be envisaged which allow the angle of incline between the massage head and the body to be changed, e.g., a conical wheel or equivalent gearing system.

In a variation shown in FIG. 28, massage device 1 includes soft skin 71 which is installed above application surface 72 of massage head 76 and covers massage nozzles 73, 74 and 75. This soft skin 71 ensures, in particular, that the nozzles are not too aggressive and improves adherence to the skin due to surface contact. This soft skin may be used with claws 49 and 50 in FIGS. 12 and 13 or various variants with nozzles or even others.

In a variation shown in FIGS. 21 and 22, massage device 1 has cosmetic product distribution system 77 which includes non-rigid product reservoir 78 on which barrette 79 pushes, which moves in the direction of arrow 80 along the length of product reservoir 78. Trigger system 81 allows barrette 79 to be moved in the direction of arrow 80. This trigger system 81 could, for example, consist of button 82 which is part of barrette 79 and move in the direction of this arrow 80 when manually triggered. Notched piece 83 holds notch 84 against button 82 each time it is pressed to hold barrette 79 in position as its advances toward product reservoir 78. Distribution system 77 includes tube 85 the location of which allows the cosmetic product to be distributed on application surface 86, either between massage elements 87 and 88, or through massage elements 87 and 88, as shown in FIG. 28. These massage elements 87 and 88 are massage wheels shown in FIG. 28; of course, they may be nozzles or claws. We see in FIG. 28 that tube 85 includes first section 85a within body 2 of the massage device and second section 85b within massage head 89. Waterproof connection mechanisms 90 is provided for between first section 85a and second section 85b of the tube. Other waterproof connection mechanisms 90 may be envisioned, for example, a male and female connection with waterproof joints.

Other cosmetic product distribution system variants are possible. In particular, one could foresee an automatic trigger system to continuously and regularly distribute, for example, to pump the cosmetic product using, e.g., an electric pump. A natural cosmetic product distribution system could also be used where the cosmetic product is regularly distributed based on physical action which does not require external triggering.

In a variation shown in FIGS. 23 and 24, distribution system 91 includes reservoir 92 which is soft and trigger 93, which includes lever 94 and motorized finger 95 configured to move in an alternating pattern in the direction of arrows 96. Distribution system 91 includes slide system 97 which has light 98 in which rear extremity 94a of lever 94 may move. Lever 94 is configured to initially be located in the position shown in FIG. 23, in which rear extremity 94a of lever 94 is positioned to the rear 98a of the light and said lever 94 is disengaged from motorized finger 95. Accordingly, manual action on lever 94 is necessary to push on reservoir 92 and distribute the cosmetic product through tube 99, which may have a configuration similar to tube 85 in FIG. 28. On the other hand, when rear extremity 94a of lever 94 is located in front of 98b of the light, as shown in FIG. 24, motorized finger 95 automatically triggers lever 94 which presses reservoir 92 and distributes the cosmetic product through tube 99. Other implementation variants of a cosmetic product distribution system with a rocking system in manual or automatic mode may be envisioned without falling outside the scope of the invention.

As shown in FIG. 25, massage device 1 includes drive 100 which is rotated along axis X16 by motor 3 using gearing system 101, which known to those familiar with the art. Extremity 100a of this drive 100 is installed in massage heads 4, 5, 6, 7 and 8, for example, on the carter 102 on the massage elements and accepts counter balance 103 which turns in irregularly around axis X16 and the massage head is vibrated when massage device 1 is applied. Other vibration system variants are possible. In particular, counter balance 103 could be placed directly within body 2 near the massage head to simplifier the design and avoid an additional connection system on drive 100 where the body and the massage head connect. The vibration system could also be integrated completely into massage head, a drive shaft activated by motor 3 or another motor, which penetrates the head, a connection system comparable to that shown in FIGS. 9 and 10 could then be envisioned, for example.

In a variation shown in FIGS. 11 and 26, massage device 1 includes on application surface 104 on massage head 105 luminescent diodes 106 which are controlled by an electronic box (not shown) installed within body 2. These luminescent diodes 106 may be lit either automatically when massage heads 4, 5, 6, 7 and 8 are activate or individually using a separate control button (not shown). Luminescent diodes 106 could, for example, be located on peripheral edge 107 of application surface 104, or on said application surface 104 outside the movement range of the massage elements. Different or multi-colored luminescent diodes could be used, depending on the wavelength and/or the treatment desired, or even a control box to change the wavelength of these luminescent diodes 106. Light transmission system 108 is installed between massage heads 4, 5, 6, 7 and 8 and body 2. This light transmission system includes fiber optic connections 109 and 110 which allow the light emitted to be directed to application surface 104 or to the massage elements, as massage nozzles.

In an implementation variation shown in FIG. 27, massage device 1 includes two electrodes 111 and 112 which have different electrical potential. These electrodes 111 and 112 may consist of in two massage elements 113 and 114 or be installed on application surface 115. These electrodes 111 and 112 are powered by electrical source 116 installed in body 2. This design allows trans-dermal ionization treatment prior to or during the application of a cosmetic product on the skin, which allows of accelerate the penetration of the cosmetic product. This cosmetic product may be distributed naturally, manually or automatically by massage device 1, or even applied directly on the skin by the user. Massage device 1 includes of removable connection mechanisms 117 and 118 which allow electrodes 111 and 112 to be quickly connected or disconnected during when massage head 120 is installed on body 2. For example, electrical contacts could be installed within installation zone 121 between massage head 120 and body 2.

As shown in FIGS. 1 and 4, massage device 1 includes installation mechanism 9 which is configured so that massage heads 4, 5, 6, 7 and 8 can be quickly installed on or removed from body 2. This installation mechanism 9 is installed using a removable fixation system between the massage head and the body. In the implementation in FIG. 4, body 2 includes notches 122 and 123 and massage heads 4, 5, 6, 7 and 8 includes piece 124 which accepts transmission mechanism 125 which moves the massage elements, connected to motor 3 through a connection system which allows the angle of incline of the massage head compared to body 2 to be adjust. This piece 124 includes notches 126 and 127 and retraction mechanism 128 and 129 of notches 126 and 127 allows them to be moved into and out of notches 122 and 123.

Figure 29:
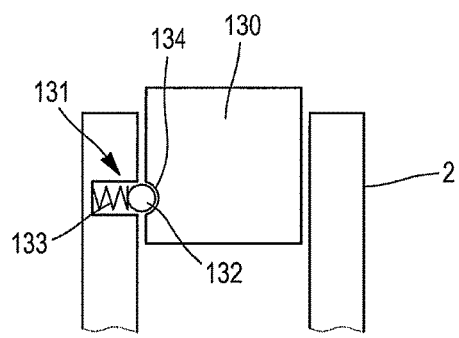
FIGS. 29 to 36 shows variants of the snap connection system between the massage head and the body.
Figure 30:
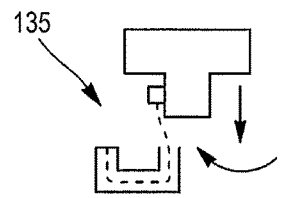
Figure 31:
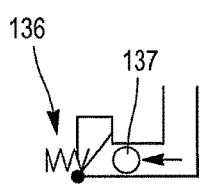
Figure 32:
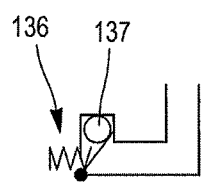
Figure 33:
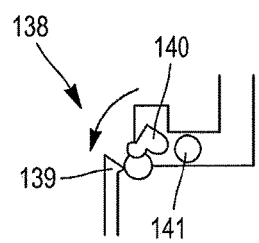
Figure 34:
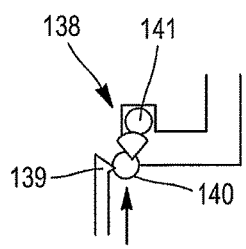
Figures 35, 36:
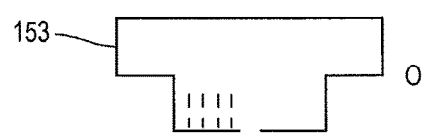

Various snapping or retraction mechanism systems are shown in FIGS. 29 to 36 to allow massage head 130 to remain installed on body 2. In FIG. 29, stop system 131 with ball 132 is shown where ball 132 is mounted on spring 133 and accepts throat 134 on massage head 130. In FIG. 30, socket system 135 is shown. In FIGS. 31 and 32 valve and spring 136 system is shown, which block piece 137, which is driven by the massage head. In FIGS. 33 and 34, blockage system 138 with notch 139 and release latch 140 is shown with piece 141 in a locked and unlocked position. In FIGS. 35 and 36, blockage system 142 allows two notches 143, 144 to lock or unlock piece 145. These various implementation variants are not limitative.

As shown in FIGS. 14 to 20, massage device 1 includes recognition means 146 of massage head 147 installed on body 2.

Figure 37:
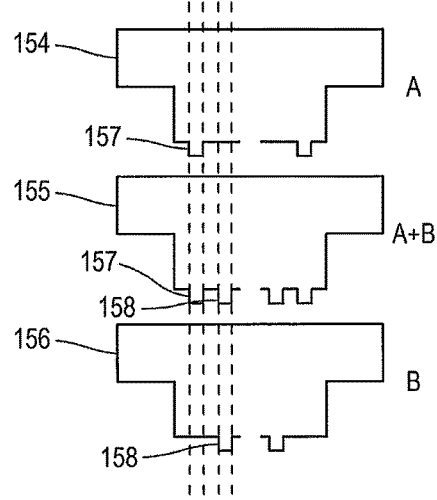
FIG. 37 shows various types of massage heads during installation on the body.

In FIGS. 14 and 15, massage head 146 includes circular protuberance 148 which is designed to move into circular groove 149 on body 2. Body 2 includes second circular groove 150. In these circular grooves 149 and 150 mechanical contacts 151 and 152 are installed. When massage head 146 is installed on body 2, protuberance 148 triggers mechanical contact 151. In FIG. 37, we see four massage heads 153, 154, 155 and 156 which may be installed on body 2. First massage head 153 does not include a protuberance. Second massage head 154 includes protuberance 157. Third massage head 155 includes two protuberances 157 and 158. Fourth massage head 156 includes protuberance 158. During installation of these massage heads 153, 154, 155 and 156 on body 2, they trigger one of two mechanical contacts 159 and 160, which allows them to be recognized based on binary code programmed into command box 161 shown in FIG. 14. This command box 161 is configured to control the various triggers present in massage device 1 based on the type of massage head installed. Accordingly, for example, command box 161 controls the motors, the cosmetic product distribution pumps, the trans-dermal ionization processing mechanism, the vibration systems, the light system, etc.

In FIG. 16, we note that protuberances 162 and 163 are located on body 2 and triggered by mechanical contacts 164 and 165 and massage head 147 includes circular groove 166.

Variants are possible within the scope of the invention. In particular, the mechanical contacts may be replace by magnetic contacts or sensors.

In FIGS. 14 and 17 to 20 optical sensors 167 are shown. In FIG. 17, massage head 147 includes transparent surface 168 which allows the light emitted by luminescent diode 169 to pass through and be detected by optic sensor 170. Therefore, the light is detected by transparency. In the variation in FIG. 18, surface 171 is opaque and sensor 170 therefore detects an opacity when massage head 147 is installed. In FIG. 19, 172 separator is installed between massage head 147 and body 2. In FIG. 20, a mirror system is installed between massage head 147 and body 2.

Other variants are possible without falling outside the scope of the invention, in particular, with respect to the recognition of the massage heads on body 2 and command box 161. For example, the sensors may allow the correct installation of massage head 147 on body 2 to be detected.

The invention claimed is:

1. Massage device (1) including:
    a body (2) which contains a drive mechanism (3),
    at least one type of massage head (4, 5, 6, 7 and 8) which includes massage elements,
    a transmission mechanism which allows the massage elements to be activated by the drive mechanism,
    an installation mechanism (9) which is configured for the installation and removal of the at least one type of massage head with the body, characterized in that the device includes recognition means (146) of the type of massage head installed on the body and control mechanisms (161) for controlling said massage device based on the recognition of the type of massage head, wherein the massage device comprises a reduction gear installed on an output of a motor, wherein the installation mechanism comprises a snapping mechanism comprising a blockage system with a notch and a release latch, wherein the recognition means comprises: (i) mechanical sensors installed on the at least one type of massage head and the body, and are configured to transfer information to the control mechanisms based on the type of massage head installed on the body; or (ii) magnetic sensors installed on the at least one type of massage head and the body, and are configured to transfer information to the control mechanisms based on the type of massage head installed on the body, and wherein the mechanical or magnetic sensors are formed in grooves of the body that receive protuberances of the at least one type of massage head such that the protuberances trigger the mechanical or magnetic sensors and are recognized based on binary code programmed into a command box.

2. Massage device (1) in accordance with claim 1, in which the recognition means (13) are the mechanical sensors (151 and 152, 164, 165).

3. Massage device (1) in accordance with claim 1, in which the recognition means (146) are the magnetic sensors.

4. Massage device (1) in accordance with claim 1, in which the recognition means (146) further comprises optical sensors (169, 170) installed on the at least one type of massage head (147) and the body (2) and are configured to transfer information to the control mechanisms (161) based on the type of massage head installed on the body.

5. Massage device (1) in accordance with claim 1, in which the control mechanisms (161) are configured to control the drive mechanism (3) and alter an action of the drive mechanism based on the type of massage head (4, 5, 6, 7 and 8) installed on the body (2).

6. Massage device (1) in accordance with claim 1, which includes a wave emission system (106) installed on the body and a wave transfer mechanism (108) to transfer waves from the emission system to the at least one type of massage head (4, 5, 6, 7 and 8).

7. Massage device (1) in accordance with claim 6, in which the control mechanisms (161) are configured to control the wave emission system (106) and alter the waves based on the type of massage head (4, 5, 6, 7 and 8) installed on the body (2).

8. Massage device (1) in accordance with claim 1, which includes a cosmetic product distribution system (77) installed on the body and a transfer mechanism (90) to transfer the product from the body (2) to the at least one type of massage head (4, 5, 6, 7 and 8).

9. Massage device (1) in accordance with claim 8, which includes a trigger mechanism (91) of the cosmetic product distribution system configured to allow the operation of said distribution system in manual or automatic mode.

10. Massage device (1) in accordance with claim 8, in which the control mechanisms (161) are configured to control the cosmetic product distribution system and alter the distribution of the cosmetic product based on the type of massage head (4, 5, 6, 7 and 8) installed on the body (2).

11. Massage device (1) in accordance with claim 1, in which the installation mechanism (9) includes a system to detect the correct installation of the at least one type of massage head (4, 5, 6, 7 and 8) on the body (2).

12. Massage device (1) in accordance with claim 1, which includes connection mechanisms between the drive mechanism (3) and the transmission mechanism configured to adjust an angle of orientation of the transmission mechanism when the at least one type of massage head (4, 5, 6, 7 and 8) is installed on the body (2).

13. Massage device (1) in accordance with claim 1, in which the at least one type of massage head (5) contains an application surface (21) and the massage elements comprise at least two massage nozzles which extend perpendicularly to the exterior of the application surface and the massage nozzles appear on the application surface in the shape of virtual concentric circles of center C and in which the transmission mechanism is configured to move the massage nozzles closer together and/or, inversely, to separate them by moving said massage nozzles in one direction and/or the other depending on the patterns which connect them to the center C.

14. Massage device (1) in accordance with claim 13, in which the at least one type of massage head (5, 6, 7 and 8) includes a soft skin (29) which covers the massage elements (22a, 22b, 22c, 24a, 24b, 26a, 26b, 26c, 28a and 28b).

15. Massage device (1) in accordance with claim 13, in which the at least one type of massage head includes a crown (56) which extends perpendicularly to the application surface and the transmission mechanism is configured to trigger an oscillation of the crown around an axis perpendicular to the application surface.

16. Massage device (1) in accordance with claim 1, in which the at least one type of massage head (6) contains an application surface (23) and the massage elements comprise two massage nozzles which extend perpendicularly to the exterior of the application surface, the transmission mechanism is configured to trigger the rotation of the two nozzles in accordance with an axis perpendicular to the application surface, with an oscillation.

17. Massage device (1) in accordance with claim 1, in which the at least one type of massage head (7) contains an application surface (25) and the massage elements comprises three massage nozzles inclined to the exterior of the application surface and the transmission mechanism is configured to trigger the rotation of the three massage nozzles in accordance with three fixed axes respective, perpendicular to the application surface.

18. Massage device (1) in accordance with claim 1, in which the at least one type of massage head (8) includes an application surface and the massage elements comprise at least two massage fingers which extend to the exterior of the application surface and the massage fingers and the transmission mechanism are configured to form a claw.

19. Massage device in accordance with claim 1, in which the at least one type of massage head (4) includes an application surface (31) and the massage elements comprise two massage wheels installed along two parallel longitudinal axes, with a gap between them, and extend partially outside the application surface in which the transmission mechanism is configured to cause synchronized and inverse rotation of the two wheels so that, when seen in a plane perpendicular to the two axes, the section of the massage wheel on the left which extends outside of the application surface turns counterclockwise and the section of the massage wheel on the right which extends outside the application surface turns clockwise.

20. Massage device (1) in accordance with claim 1, which includes a trans-dermal ionization treatment mechanism which is configured to transfer a current on a skin during the application of said massage device to increase and/or accelerate the penetration of a cosmetic product.

* * * * *